United States Patent [19]

Rupp et al.

[11] Patent Number: 5,696,171
[45] Date of Patent: Dec. 9, 1997

[54] CONTACT LENS DISINFECTING COMPOSITIONS AND METHODS EMPLOYING TERPENES

[75] Inventors: David C. Rupp, San Pedro; Terrence J. Hunt, Anaheim, both of Calif.

[73] Assignee: Allergan, Inc., Irvine, Calif.

[21] Appl. No.: 298,508

[22] Filed: Aug. 30, 1994

[51] Int. Cl.$^6$ .................................................. A61K 31/11
[52] U.S. Cl. .................................... 514/700; 514/912
[58] Field of Search ................................... 514/700, 912

[56] References Cited

U.S. PATENT DOCUMENTS

| | | | |
|---|---|---|---|
| 4,758,595 | 7/1988 | Ogunbiyi et al. | 514/635 |
| 5,312,820 | 5/1994 | Ashton et al. | 514/227.5 |

FOREIGN PATENT DOCUMENTS

| | | |
|---|---|---|
| 91-298962 | 8/1991 | Japan. |
| 94/00160 | 1/1994 | WIPO. |

OTHER PUBLICATIONS

Anke et al., "Assays of the Biological Activities of Guaiane Sesquiterpenoids Isolated from the Fruit Bodies of Edible Lacterius Species," *Fd. Chem. Toxic.* 27 (No. 6): 393–397 (1989) (UK).

Anke et al., "Structure–Activity Relationships for Unsaturated Dialdehydes," *J. Antibiotics* 42 (No.5): 738–744 (1989).

Anke et al., "Comparison of the Antimicrobial and Cytotoxic Activities of Twenty Unsaturated Sesquiterpene Dialdehydes from Plants and Mushrooms," *Planta Med.* 57:344–345 (1991)

Atzori et al., "Activity of Bilobalide, a Sesquiterpene from *Ginkgo biloba*, on *Pneumocystis carinii*," *Antimicrobial Agents and Chemotherapy* 37 (No. 7): 1492–1496 (US) (1993).

Meshnick et al., "Iron–Dependent Free Radical Generation from the Antimalarial Agent Artemisinin (Qinghaosu)," *Antimicrobial Agents and Chemotherapy*, May 1993, pp. 1108–1114.

Abstract of WO9317558, (1993).

*Primary Examiner*—Zohreh Fay
*Attorney, Agent, or Firm*—Jeffer, Mangels, Butler & Marmaro LLP

[57] ABSTRACT

A disinfecting composition for contact lenses includes an effective disinfecting amount of a terpene or combination of terpenes.

4 Claims, No Drawings

CONTACT LENS DISINFECTING COMPOSITIONS AND METHODS EMPLOYING TERPENES

BACKGROUND OF THE INVENTION

1. Field of the Invention

This invention relates to compositions and methods for disinfecting contact lenses. More specifically, the present invention is directed to a composition comprising an effective disinfecting amount of a terpene, particularly a sesquiterpene ($C_{15}$).

2. Description of Related Art

The growth of the contact lens industry has led to a dramatic increase in the number of lenses and care regimens in the marketplace. Designing care regimens to meet the needs of all possible permutations has become a challenge to the industry. In particular, a goal of the lens care industry is to simplify the lens care regimen to obtain greater patient compliance.

Contact lenses, especially those made from hydrophilic materials, must be continuously disinfected to kill any harmful microorganisms that may be present or grow on the lenses. Microorganisms that are incorporated in the panel of microorganisms required by the 1985 U.S. FDA guidelines for contact lens solutions for disinfection efficacy include *Serratia marcescens* ("S.M.") (ATCC 14041), *Staphylococcus epidermidis* ("S.E.") (ATCC 17917), *Pseudomonas aeruginosa* ("P.A.") (ATCC 15442) and *Candida albicans* ("C.A.") (ATCC 10231).

A number of methods for disinfecting contact lenses have been described, such as the use of high temperatures, the use of oxidative chemicals, and the use of antimicrobial agents. U.S. Pat. Nos. 4,407,791 and 4,525,346 show the polyquaternary ammonium contact lens disinfecting agent 1-tris (2-hydroxyethyl) ammonium-2-butenyl-4-poly [1-dimethyl ammonium-2-butenyl]-ω-tris (2-hydroxyethyl) ammonium chloride salt. European patent application 89810477.3 discloses the disinfecting agent dodecyl-dimethyl-(2-phenoxyethyl)-ammonium bromide. U.S. Pat. No. 4,029,817, assigned to Allergan, Inc., shows the contact lens disinfecting agent tallow triethanol ammonium chloride. U.S. Pat. No. 4,758,595 describes the hexamethylene biguanide contact lens disinfecting agent.

A need exists for new agents useful in disinfecting contact lenses, in particular "broad spectrum" agents which are effective against a wide variety of bacteria and fungi. Such compounds desirably should show low toxicity. Compounds produced by plants or fungi, for example, would be particularly beneficial in that such compounds can be considered "natural ingredients" in contact lens disinfecting compositions. Beneficially, such compounds should also be useful in combination with other known disinfecting agents and with enzymes, such as proteolytic enzymes, which are useful for removal of deposits from contact lenses.

SUMMARY OF THE INVENTION

In accordance with one aspect of the present invention, a disinfecting composition is provided which comprises an effective disinfecting amount of at least one terpene. Terpenes useful according to the invention are those having anti-bacterial, anti-fungal or algaecidal activity. In a preferred embodiment, the terpene is a sesquiterpene ($C_{15}$).

The terpene can be used alone or in combination, as well as in combination with other disinfecting agents. The terpenes can also be used in conjunction with non-oxidative or oxidative systems of disinfection, and with enzymes, such as proteolytic enzymes.

In accordance with another aspect of the present invention, a method of disinfecting a contact lens is provided which comprises the step of contacting the lens with an effective disinfecting amount of a terpene or combination of terpenes.

In accordance with a further aspect of the present invention, a method of producing a contact lens disinfecting composition is provided which comprises the step of adding to a liquid carrier an effective disinfecting amount of a terpene or combination of terpenes.

Other objects, features and advantages of the present invention will become apparent to those skilled in the art from the following detailed description. It is to be understood, however, that the detailed description and specific examples, while indicating preferred embodiments of the present invention, are given by way of illustration and not limitation. Many changes and modifications within the scope of the present invention may be made without departing from the spirit thereof, and the invention includes all such modifications.

DETAILED DESCRIPTION OF THE INVENTION

The present invention can be used with all contact lenses such as conventional hard, soft, rigid, gas permeable, and silicone lenses but is preferably employed with soft lenses such as those commonly referred to as hydrogel lenses prepared from monomers such as hydroxyethyl methacrylate, hydroxyethylmethyl methacrylate, vinylpyrrolidone, glycerol methacrylate, methacrylic acid or acid esters and the like. Hydrogel lenses typically absorb significant amounts of water such as from 38 to 80 percent by weight.

The terpene, preferably sesquiterpene, compounds useful according to the present invention have anti-bacterial, anti-fungal and/or algaecidal activity. The compounds show low cytotoxicity. Some compounds, such as bilobalide, have in addition been reported to show anti-oxidant activity (i.e., act as free radical scavengers). Many are produced by plants or fungi, and thus can be considered as "natural ingredients" in eye care products.

Exemplary terpene compounds, including sesquiterpene compounds and terpene derivatives, within the scope of the invention include: camphor; carvacrol; caryophyllene (from cloves); citral; d-limonene (orange oil, lemon oil); farnesol (from lily of the valley); geraniol (from roses and other flowers); ionone; linalool; menthol (from peppermint); myrcene (from bayberry wax, oil of bay and verbena); neral; α-, β-pinene oil (oil of turpentine); retinal; retinoic acid; b-selinene (from celery); terpinene; α-terpineol; thymol; vitamin A; and zingiberene (from ginger).

Further naturally produced terpenes which are useful according to the invention include avarol; bilobalide; deterol; epipolygodial; isometachromin; isovelleral; lactardial; lactaroviolin; lentinellic acid; marasmic acid; merulidial; pilatin; polygodial; and velleral. Anke et al., *Planta Med.* 57: 344–345 (1991), and Atzori et al., *Antimicrobial Agents and Chemotherapy* 37 (No. 7): 1492–1496 (1993), the contents of which are incorporated herein by reference, describe a number of the foregoing compounds, in particular velleral, isovelleral, polygodial, methyl marasmate and bilobalide.

Other terpene compounds which can be useful according to the invention include those described in Anke et al., *Fd.*

*Chem. Toxic.* 27 (No. 6): 393–397 (1989) (lactaroviolin, deterrol); Anke et al., *J. Antibiotics* 42 (No. 5): 738–744 (1989) (merulidial and its derivatives); Didry et al., *Pharmazie*, April 1993, 48(4): 301–304 (cinnamaldehyde); Gundidza et al., *Cent. Afr. J. Med.*, July 1992, 38(7): 290–293 (Zimbabwe) (terpenes contained in oil of *Haslundia opposita*); and Himejima et al., *J. Nat. Prod.* 55(5): 620–625 (May 1992) (extract of seeds of *Licaria puchurimajor*). The contents of all of the foregoing references are incorporated herein in their entireties by reference.

Terpene derivatives, such as sesquiterpene derivatives described in the foregoing references (e.g., acetylated or methylated compounds), are also useful according to the invention. A "derivative" of a terpene as used herein denotes a terpene having one or more substituents, such as alkyl groups, carboxyl groups, hydroxyl groups, or other moieties. Preferably, such substituents do not reduce the effectiveness of the terpene as a disinfectant.

Additional useful sesquiterpene derivatives include compounds such as artemisinin (a sesquiterpene lactone having a peroxide moiety) and related compounds as described in Meshnick et al., *Antimicrobial Agents and Chemotherapy*, May 1993, pp. 1108–1114, the contents of which are incorporated herein by reference. Certain of the derivatives described in the cited references actually possess enhanced anti-microbial activity.

One or more terpenes are employed according to the invention in an effective disinfecting amount. An effective disinfecting amount of a disinfecting agent or combination of disinfecting agents is an amount which will at least partially reduce the microorganism population in the solutions employed. Preferably, an effective disinfecting amount is that amount which will reduce the microbial burden by two log orders in four hours and more preferably by one log order in one hour for all organisms with the exception of *A. fumigatus*. Most preferably, an effective disinfecting amount is an amount which will eliminate the microbial burden on a contact lens when used in a contact lens care regimen which includes a recommended soaking time (FDA Chemical Disinfection Efficacy Test-July, 1985 Contact Lens Solution Draft Guidelines, incorporated herein by reference).

Typically, the terpene or combination of terpenes is present in the working solution in a concentration ranging from about 0.00001 to 1.0% (w/v), preferably about about 0.0001 to 0.1% (w/v).

The terpenes, preferably sesquiterpenes, useful according to the present invention can be employed alone or in combination. In an alternative embodiment, the terpenes can be employed together with other compatible disinfecting agents. For example, numerous non-oxidative organic chemicals which derive their activity through a chemical or physiochemical interaction with microorganisms can be used in conjunction with one or more terpenes. Oxidative systems, such as hydrogen peroxide systems and systems based on the use of hydroxyl radicals, can also be employed. The additional disinfectant or disinfectants preferably should not interact with the selected terpene or combination of terpenes in a manner which decreases the effectiveness of either type of compound.

Suitable additional disinfecting agents are those generally employed in ophthalmic applications and include, but are not limited to, quaternary ammonium salts used in ophthalmic applications such as poly[(dimethylimino)-2-butene-1,4-diyl chloride, α-[4-tris(2-hydroxyethyl) ammonium-2-butenyl-ω-tris(2-hydroxyethyl)ammonium]-dichloride (chemical registry number 75345-27-6) generally available as polyquaternium 1® from ONYX Corporation, benzalkonium halides, and biguanides such as salts of alexidine, alexidine free base, salts of chlorhexidine, hexamethylene biguanides and their polymers. See U.S. Pat. No. 4,758,595, which is incorporated herein by reference.

The salts of alexidine and chlorhexidine can be either organic or inorganic and are typically disinfecting nitrates, acetates, phosphates, sulfates, halides and the like. Generally, the hexamethylene biguanide polymers, also referred to as polyaminopropyl biguanide (PAPB), have molecular weights of up to about 100,000. Such compounds are known and are disclosed in U.S. Pat. No. 4,758,595.

Another compound which meets the foregoing criteria when detoxified is a compound having the following formula. See U.S. Pat. No. 4,029,817, assigned to Allergan, Inc., which is incorporated herein by reference.

In formula I, R is an alkyl or alkenyl radical having 12–20 carbon atoms and preferably a tallow radical, i.e., composed of mixtures of —$C_{17}H_{34}$ and —$C_{17}H_{35}$; and $R_1$, $R_2$, and $R_3$ are the same or different and represent alkyl radicals having 1–3 carbon atoms. This compound should be used together with a detoxifying amount of a non-toxic compound selected from the group consisting of water soluble polyhydroxyethyl methacrylate, carboxymethylcellulose, non-ionic surfactants such as polyoxyethylene sorbitan fatty acid esters and polyoxyethylene ethers, polyvinylpyrrolidone, polyvinyl alcohol, hydroxypropylmethylcellulose and mixtures thereof.

The preferred compound of formula I is alkyl triethanol ammonium chloride wherein the alkyl group is a tallow radical. This compound is known as Miramine TA-30® and is commercially available from the Miranol Chemical Company. The preferred compound can be obtained as a 30% aqueous acidic solution. The compound is fairly stable in acidic pH but tends to precipitate out of solution as the base under alkaline conditions.

The compounds which act to detoxify the active ingredient of formula I, yet allow the active ingredient to retain its bactericidal properties, are one or more of the following detoxifying compounds: water soluble polyhydroxyethyl methacrylate, carboxymethylcellulose, non-toxic, non-ionic surfactants, polyvinylpyrrolidone, polyvinyl alcohol and hydroxypropylmethylcellulose. The preferred compounds are the water soluble polyhydroxyethylmethacrylate, sodium carboxymethylcellulose and the non-toxic, non-ionic surfactants such as polyoxyethylene (20) sorbitan monooleate or Polysorbate 80, also known as "Tween 80."

The water soluble polyhydroxyethylmethacrylate described above is soluble in alkaline water, the solubility varying with the alkalinity of the water and also on the degree of polymerization. The preferred grade is the polymer with an average molecular weight of about 60,000 to 700,000 and preferably having an average molecular weight of about 80,000 to 225,000. These polymers are available from Hydron Laboratories, e.g. under the trademark "Hydron Biomedical Polymer, Type A1."

Carboxymethylcellulose or sodium carboxymethylcellulose is a synthetic cellulose gum containing 0.4 to 1.5 sodium carboxymethyl groups (—$CH_2COONa$) per glucose unit of the cellulose. It is a white, odorless, non-toxic hygroscopic powder readily dispersible in hot or cold water. The pH of a 1% solution is 6.5–8.0.

The detoxifying agents which are described as non-toxic, non-ionic surfactants are surfactants such as the polyoxyethylene sorbitan fatty acid ester, e.g. the "Tween" series of surfactants, as exemplified by Polysorbate 80; and polyoxyethylene ethers, e.g. the "Brij" series of surfactants, as exemplified by "Brij 57". Polysorbate 80, otherwise described as polyoxyethylene (20% sorbitan monooleate) is an oleate ester of sorbitol and its anhydrides copolymerized with approximately 20 moles of ethylene oxide for each mole of sorbitol and sorbitol anhydrides. Polysorbate 60 is available commercially from Atlas Chemical Company under the name "Tween 80". "Brij 56," also a trade name of Atlas Chemical Company, is polyoxyethylene (20) cetyl ether. The other well-known members of the "Tween" and "Brij" series of surfactants may also be used in the present invention.

The amount of the detoxifying compounds which may be used in connection with the disinfecting agent of formula I varies from about 0.0001 to about 2.0% (w/v) and preferably from about 0.04 to about 0.4% (w/v) of the aqueous working solution.

Another additional disinfecting agent useful with terpenes is the poly quaternary amine Croquat L. Croquat L is a quaternary ammonium substituted polypeptide which is based on a collagen hydrolysate of relatively low molecular weight, includes lauryl trimethyl ammonium chloride groups and has a molecular weight in the range of 500 to about 5000. Croquat L is commercially available from Croda, Inc.

A useful quaternary ammonium substituted polypeptide disinfecting agent has the following formula

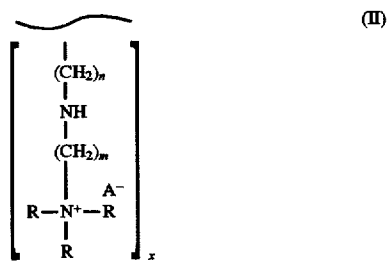

(II)

wherein the wavy line represents a polypeptide backbone; n is an integer in the range of 1 to about 5, preferably 2; m is an integer in the range of 1 to about 30, preferably about 10 to about 20; each R is independently selected from alkyl groups containing 1 to about 20 carbon atoms; $A^-$ is selected from ophthalmically acceptable anions; and x represents the number of bracketed groups interspersed along the polypeptide backbone and is an integer in the range of 1 to about 20, preferably about 2 to about 6. In one embodiment, at least one R is methyl and one other R contains about 8 to about 20 carbon atoms. In another embodiment, each of the R's is methyl, and m is in the range of about 10 to abut 20.

Examples of ophthalmically acceptable anions include chloride ($Cl^-$), bromide, iodide, sulfate, bisulfate, phosphate, acid phosphate, nitrate, acetate, maleate, fumarate, oxalate, lactate, tartrate, citrate, gluconate, saccharate, p-toluene sulfonate and the like. The preferred ophthalmically acceptable anion is $Cl^-$.

Yet another group of additional disinfecting agents are water soluble cationic polymers (WSCPs). The presently useful water soluble cationic polymers preferably have the following repeating unit

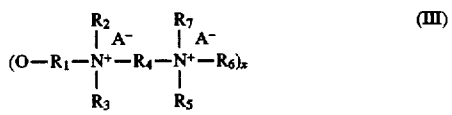

(III)

wherein $R_1$, $R_4$ and $R_6$ are each independently selected from alkylene radicals containing 1 to about 6 carbon atoms. $R_2$, $R_3$, $R_5$ and $R_7$ are each independently selected from alkyl radicals containing 1 to about 6 carbon atoms, each $A^-$ is independently selected from ophthalmically acceptable anions, and x is the number of repeating units in the polymer and is an integer in the range of about 5 to about 30. A particularly useful quaternary ammonium polymer has the following repeating unit

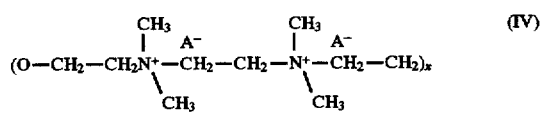

(IV)

The number of repeating units per polymer molecule, represented by x, is more preferably about 8 to about 30, especially about 14.

Examples of ophthalmically acceptable anions include chloride ($Cl^-$), bromide, iodide, bisulfate, phosphate, acid phosphate, nitrate, acetate, maleate, fumarate, oxalate, lactate, tartrate, citrate, gluconate, saccharate, p-toluene sulfonate and the like. The preferred ophthalmically acceptable anion is $Cl^-$.

In one particularly useful embodiment, the quaternary ammonium polymer has a molecular weight in the range of about 500 to about 5000.

A specific example is poly [oxyethylene (dimethyliminio) ethylene-(dimethyliminio) ethylene dichloride] ("WSCP(1)") as shown in below.

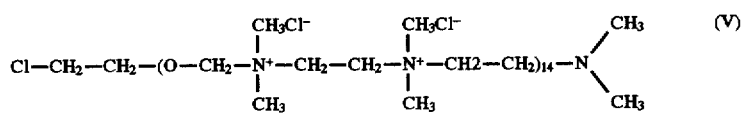

(V)

WSCP disinfecting agents are commercially available from Buckman Laboratories, Inc. and are described in U.S. Pat. No. 4,250,269, which is incorporated herein by reference.

Other useful additional disinfecting agents include dodecyl-dimethyl-(2-phenoxyethyl)-ammonium bromide.

In addition to being combined with one or more additional disinfecting agents, the terpenes, preferably sesquiterpenes, useful according to the present invention can be combined with one or more agents for the removal of lens deposits. In the normal course of wearing contact lenses, tear film and debris consisting of proteinaceous, oily, sebaceous, and related organic matter have a tendency to deposit and build up on lens surfaces. As part of the routine care regimen, contact lenses must be cleaned to remove these tear film deposits and debris. If these deposits are not properly removed, both the wettability and optical clarity of the lenses is substantially reduced causing discomfort for the wearer.

The only safe and effective means found to date for removing protein build-up is the use of enzymes, whose hydrolytic activity reduces the proteinaceous materials to small, water soluble subunits. Particularly useful are proteolytic enzymes or proteases. For example, U.S. Pat. No. 3,910,296 discloses the use of proteases for cleaning contact lenses. One or more enzymes, such as proteases, can be used together with one or more terpenes to disinfect and clean contact lenses according to the present invention.

The proteolytic enzymes used herein must have at least a partial capability to hydrolyze peptide-amide bonds which reduces the proteinaceous material to smaller water-soluble subunits. Typically, these enzymes will exhibit some lipolytic, amylolytic or related activities associated with the proteolytic activity and may be neutral, acidic or alkaline. In addition, separate lipases or carbohydrases may be used in combination with the proteolytic enzymes as well as thermally stable proteases.

A thermally stable protease or thermophilic enzyme denotes a protease that is stable and active at temperatures higher than 70° C. or even higher than 100° C. One such heat stable protease is thermolysin. Reference may be had to pages 642–650 of Perlmann et al., "Proteolytic Enzymes," Methods in Enzymology, Volume XIX, Academic Press (1970).

The protease employed in accordance with the invention may be selected from those enzymes which are conventionally employed in the enzymatic cleaning of contact lenses. For example, many of the enzymes disclosed in Huth et al., U.S. Reissue Pat. No. 32,672, and Karageozian et al., U.S. Pat. No. 3,910,296, are useful in the present invention. These patents are incorporated in their entirety by reference herein. Microbial derived enzymes are also disclosed in U.S. Pat. No. 4,690,773, which is incorporated herein by reference.

A preferred group of proteases are the derived alkaline proteases generically called subtilisin enzymes. Reference is made to Keay et al., "Proteases of the Genus Bacillus. II Alkaline Proteases", Biotechnology and Bioengineering, Vol. XII, pp 213–249 (1970) and Keay et al., "Differentiation of Alkaline Proteases from Bacillus Species," Biochemical and Biophysical Research Comm., Vol. 34, No. 5, pp. 600–604 (1969).

The subtilisin enzymes include two sub-classes, subtilisin A and subtilisin B. In the subtilisin A grouping are enzymes derived from such species as *B. subtilis*, *B. licheniformis* and *B. pumilis*. Organisms in this sub-class produce little or no neutral protease or amylase. The subtilisin B sub-class includes enzymes from such organisms as *B. subtilis*, *B. subtilis* var. *amylosacchariticus*, *B. amyloliquefaciens* and *B. subtilis* NRRL B3411. These organisms produce neutral proteases and amylases on a level about comparable to their alkaline protease production. Generally, the preferred enzymes are active proteolytic enzymes, with the most preferred being subtilisin A.

In addition other preferred enzymes are, for example, papain, pancreatin, trypsin, chymotrypsin, pepsin, streptokinase, streptodornase, ficin, carboxypeptidase, collagenase, keratinase, carboxylase, aminopeptidase, elastase, chymopapain, bromelin, aspergillo-peptidase A and B, pronase E (from *S. griseus*) and dispase (from *B. polymyxa*). If papain is used, it is also necessary to use a reducing agent and a chelating agent, both of which are discussed below.

Metallo-proteases, those enzymes which contain a divalent metal ion such as calcium, magnesium or zinc bound to the protein, may also be used.

The identification, separation and purification of enzymes is an old art. Many identification and isolation techniques exist in the general scientific literature for the isolation of enzymes, including those enzymes having proteolytic and mixed proteolytic/amylolytic or proteolytic/lipolytic activity. The enzymes contemplated by this invention can be readily obtained by known techniques from plant, animal or microbial sources.

With the advent of recombinant DNA techniques, it is anticipated that new sources and types of stable proteolytic enzymes will become available. Such enzymes should be considered to fall within the scope of this invention so long as they meet the criteria for stability and activity set forth herein. See Japanese Laid Open Application No. J6 0030-685 for one example of the production of proteases by recombinant DNA from *Bacillus subtilis*.

An effective amount of enzyme is to be used in the practice of this aspect of the present invention. An effective amount is that amount which effects removal from a lens in a reasonable time (for example overnight) of substantially all of at least one type of debris due to normal wear. This standard is stated with reference to contact lens wearers with a history of normal pattern of lens debris accretion, not the very small group who may at one time or another have a significantly increased rate of debris accretion such that cleaning is recommended every day, or every two or three days.

The amount of enzyme required to make an effective cleaner will depend on several factors, including the inherent activity of the enzyme.

As a basic yardstick, the working solution should contain sufficient enzyme to provide about 0.001 to about 3 Anson units of activity, preferably about 0.01 to about 1 Anson unit, per single lens treatment. Higher or lower amounts may be used. Appropriate amounts are readily determined by the skilled artisan through routine testing.

Since, as noted, enzyme activity is pH dependent, the enzyme selected for use in a composition according to the invention should be effective at neutral pH.

Compositions including terpene, preferably sesquiterpene, disinfecting agents useful according to the present invention can be prepared in a number of conventional forms, such as liquid solutions, tablets, powders, etc. For example, disinfecting solutions can be prepared by adding an effective amount of at least one terpene as discussed herein to a suitable liquid carrier. Combined disinfecting and cleaning compositions can be prepared by mixing two components, i.e., dissolving the enzyme, typically in tablet form, in a solution containing the disinfecting agent. However, other methods of combining the active components as well as off-the-shelf compositions containing some or all of the active components are contemplated as being within the scope of this invention.

If an enzyme is employed in a composition according to the invention, it may be employed in liquid or solid form in combination with a reducing agent and additional components. Preferably, the enzymes and other agents are provided in solid form such as tablets or powders which are mixed with a suitable liquid carrier (e.g., water, saline solution, etc.) or a disinfecting solution.

A reducing agent may be present in the working solution and in such case would preferably be incorporated into the enzyme tablet. The reducing agent is generally any non-toxic reducing agent, either dry or liquid, depending in part upon whether the delivery system is tablet or solution. Although thiols are preferred and N-acetylcysteine more preferred, reducing agent sources generally include thiolcontaining water-soluble lower alcohols, organic carboxylic acids, organic amines and salts thereof, amino acids and di- or tripeptides, e.g. cysteine hydrochloride ethyl ester, glutathione, homocysteine, carbamoyl cysteine, cysteinylglycine, 2-mercaptopropionic acid, 2-mercaptopropionylglycine, 2-mercaptoethylamine hydrochloride, cysteine, β-mercaptoethanol, cysteine hydrochloride, dithiothreitol, dithioerythritol, sodium bisulfate, sodium metabisulfite, thiourea, sulfites, pyrosulfites and dithionites such as the alkali metal salts or alkaline earth metal salts of sulfurous acid, pyrosulfurous acid and dithionous acid, e.g. lithium, sodium, calcium and magnesium salts and mixtures thereof.

In general, in weight to volume terms, the reducing agent will be used in amounts between 0.05% and 10% of the final working solution, with 0.3% to 1.5% preferred and 0.3% to 0.5% optimal. With the most preferred reducing agent, N-acetylcysteine, used with from 0.0008 to 0.036 Anson units of subtilisin A, the range is preferably from 0.1% to 1.0% (w/v).

Additional components may be added to or incorporated into the enzyme tablets or liquid, or working solution. For example, components such as effervescing agents, stabilizers, buffering agents, chelating and/or sequestering agents, coloring agents, tonicity adjusting agents, surfactants and the like can be employed. In addition, binders, lubricants, carriers, and other excipients normally used in producing tablets may be incorporated into the enzyme tablet when enzyme tablets are employed.

Examples of suitable buffering agents which may be incorporated into an enzyme tablet or working solution include, but are not limited to, alkali metal salts such as potassium or sodium carbonates, acetates, borates, phosphates, citrates and hydroxides, and weak acids such as acetic and boric acids. Other buffers include amino acid buffers and tromethamine, also known as 2-amino-2-hydroxymethyl-1,3-propanediol. Preferred buffering agents are alkali metal borates such as sodium or potassium borates. Additionally, other pH adjusting agents may be employed such as inorganic acids. For example, hydrogen chloride may be employed in concentrations suitable for ophthalmic uses. Generally, buffering agents are present in amounts from about 0.01 to about 2.5% (w/v) and preferably, from about 0.5 to about 1.5% (w/v), of the working solution.

Effervescing agents are typically employed when the enzyme is provided in solid form. Examples of suitable effervescing agents include, but are not limited to, tartaric or citric acid used in combination with a suitable alkali metal salt such as sodium carbonate.

The tonicity adjusting agent which may be a component of the disinfecting solution and may optionally be incorporated into an enzyme tablet is employed to adjust the osmotic value of the final cleaning and disinfecting solution to more closely resemble that of human tears and to maintain a suitable level for optimum activity by the antimicrobial agent.

Suitable surfactants can be either cationic, anionic, non-ionic or amphoteric. Preferred surfactants are neutral or nonionic surfactants which may be present in amounts up to 5% (w/v). Examples of suitable surfactants include, but are not limited to, polyethylene glycol esters of fatty acids, polyoxypropylene ethers of $C_{12}-C_{18}$ alkanes, polyoxyethylene, polyoxypropylene block copolymers of ethylene diamine (i.e., poloxamine), polyoxypropylene-polyoxyethylene glycol nonionic block polymers (i.e., Pluronic polyols such as Pluronic F-127) and p-isooctylpolyoxyethylene phenol formaldehyde polymers (i.e., Tyloxapol).

Examples of preferred chelating agents include ethylenediaminetetraacetic acid (EDTA) and its salts (disodium) which are normally employed in amounts from about 0.025 to about 2.0% (w/v). Other known chelating agents (or sequestering agents) such as certain polyvinyl alcohols can also be employed.

The binders and lubricants for enzyme tableting purposes and other excipients normally used for producing powders, tablets and the like, may be incorporated into enzyme tablet formulations.

In practicing a method of the invention which employs both terpene disinfecting agents and enzymes, the enzyme formulation, either in solid or liquid form, can be dissolved a predetermined amount of a solution containing the disinfecting agent(s), typically 5-10 mL where a lens vial is used or 0.8 to 3.5 mL where the lens well of a lens case is used. The solution may be isotonic or hypotonic. This solution is then contacted with lenses at ambient temperatures for a sufficient time to clean and disinfect the lenses for safe use in the eye.

In a particular embodiment of the invention, an enzyme tablet is dissolved in an aqueous thimerosal-free multipurpose and disinfecting agent solution containing WSCP as the disinfecting agent. The lenses are then contacted with the resulting cleaning and disinfecting solution, preferably by being immersed therein, and remain in contact with the solution for a sufficient period of time to clean and disinfect the lenses. Typically, the cleaning and disinfecting will take less than about eight hours with about 1 to about 4 hours being preferred.

Preferably, the lenses can be removed from the solution and placed directly into the eye without the need for a separate neutralizing step. The lenses are rinsed with the same aqueous multipurpose and disinfecting agent solution containing the disinfecting agent prior to insertion into the eye. There is preferably no need for a separate saline solution rinsing. Thus the multipurpose and disinfecting agent solution is preferably ophthalmically acceptable, i.e., it can be placed into a human eye without causing any substantial damage or harm.

The sequence of steps for combining the components to make up the solution which contacts the lenses will vary with the physical characteristics of the components employed. However, the order of addition is not critical to the practice of this invention. For example, the enzyme could be separately formulated as a tablet or powder.

It is convenient to formulate the enzyme and other dry components as a powder or tablet and to dissolve such material in the multipurpose disinfecting agent solution, then introduce the lenses into this solution. The lenses could already be in the multipurpose disinfecting agent solution when the enzyme (in aqueous form) is introduced.

The invention is further described with reference to the following non-limiting examples. In the examples, the listed ingredients are added to an appropriate liquid carrier in the amounts indicated.

EXAMPLE 1

| Ingredient | % (w/v) |
| --- | --- |
| Polyhexamethylene biguanide, Cosmocil CQ | 0.0001 |
| Edetate disodium USP | 0.05 |
| Polygodial | 0.1 |

EXAMPLE 2

| Ingredient | % (w/v) |
|---|---|
| Polyhexamethylene biguanide, Cosmocil CQ | 0.0001 |
| Edetate disodium USP | 0.05 |
| Polygodial | 0.1 |
| Tromethamine | 1.20 |
| Tyloxapol USP | 0.025 |

EXAMPLE 3

| Ingredient | % (w/v) |
|---|---|
| Polyhexamethylene biguanide, Cosmocil CQ | 0.0001 |
| Edetate disodium USP | 0.05 |
| Velleral | 0.1 |
| Tromethamine | 1.20 |
| Tyloxapol USP | 0.025 |

EXAMPLE 4

| Ingredient | % (w/v) |
|---|---|
| Hydroxyethyl cellulose, NF | 0.65 |
| Sodium chloride | 0.67 |
| Boric acid, NF | 0.39 |
| Sodium borate decahydrate, NF | 0.20 |
| Edetate disodium | 0.127 |
| Bilobalide | 0.1 |

EXAMPLE 5

| Ingredient | % (w/v) |
|---|---|
| Hydroxyethyl cellulose, NF | 0.65 |
| Sodium chloride | 0.67 |
| Boric acid, NF | 0.39 |
| Sodium borate decahydrate, NF | 0.20 |
| Edetate disodium | 0.127 |
| Isovelleral | 0.05 |
| WSCP | 0.006 |

EXAMPLE 6

| Ingredient | % (w/v) |
|---|---|
| Hydroxyethyl cellulose, NF | 0.65 |
| Sodium chloride | 0.67 |
| Boric acid, NF | 0.39 |
| Sodium borate decahydrate, NF | 0.20 |
| Edetate disodium | 0.127 |
| Methyl marasmate | 0.05 |
| WSCP | 0.006 |
| Croquat L | 0.010 |

The following examples illustrate tablet formulations according to the invention.

EXAMPLE 7

| Ingredient | mg per tablet |
|---|---|
| Di-Pac* | 40.0 |
| Polyethylene glycol 3350 | 4.0 |
| Povidone, PVP k-30 | 4.0 |
| Merulidial | 50.0 |

*Di-Pac is a compressible sugar. It is comprised of 97 w/w % sucrose and 3 w/w % maltodextrin. Di-Pac is available from Amstar Sugar Corporation and is distributed by Austin Chemical Co. in Illinois.

EXAMPLE 8

| Ingredient | mg per tablet |
|---|---|
| Di-Pac* | 40.0 |
| Sodium perborate | 50.0 |
| Subtilisin A** | 1.042 |
| Polyethylene glycol 3350 | 4.0 |
| Povidone, PVP k-30 | 4.0 |
| Citral | 50.0 |

**Subtilisin A MG 1.5 (Novo Industries of Copenhagen, Denmark) 1.9 Au/g; 0.00198 Au/Tablet incl. 10% overage.

What is claimed is:

1. A disinfecting composition comprising (i) an effective contact lens disinfecting amount of a terpene or combination of terpenes selected from the group consisting of velleral, polygodial, methyl marasmate, bilobalide and artemisinin, (ii) at least one agent selected from the group consisting of an oxidative system and an enzyme, and (iii) a liquid carrier.

2. The disinfecting composition of claim 1 comprising about 0.00001 wt % to 1.0 wt % of said terpene or combination of terpenes.

3. A method of disinfecting a contact lens comprising the step of contacting the lens with a disinfecting composition comprising (i) an effective contact lens disinfecting amount of at least one terpene selected from the group consisting of velleral, polygodial, methyl marasmate, bilobalide, artemisinin and combinations thereof, (ii) at least one agent selected from the group consisting of an oxidative system and an enzyme, and (iii) a liquid carrier.

4. The method of claim 3 wherein said composition comprises about 0.00001 wt % to 1.0 wt % of said at least one terpene.

* * * * *